United States Patent
De Francesco

(10) Patent No.: US 11,684,684 B2
(45) Date of Patent: Jun. 27, 2023

(54) SELF-CLEANING DOOR HANDLE

(71) Applicant: Motional AD LLC, Boston, MA (US)

(72) Inventor: Daniele De Francesco, Lexington, MA (US)

(73) Assignee: Motional AD LLC, Boston, MA (US)

( * ) Notice: Subject to any disclaimer, the term of this patent is extended or adjusted under 35 U.S.C. 154(b) by 355 days.

(21) Appl. No.: 17/012,043

(22) Filed: Sep. 3, 2020

(65) Prior Publication Data

US 2022/0062465 A1 Mar. 3, 2022

(51) Int. Cl.
*A61L 2/10* (2006.01)
*A61L 2/24* (2006.01)
*E05B 85/10* (2014.01)
*G05D 1/00* (2006.01)

(52) U.S. Cl.
CPC ............. *A61L 2/10* (2013.01); *A61L 2/24* (2013.01); *E05B 85/10* (2013.01); *A61L 2202/11* (2013.01); *A61L 2202/14* (2013.01); *G05D 1/0088* (2013.01); *G05D 2201/0212* (2013.01)

(58) Field of Classification Search
CPC ..... A61L 2/10; A61L 2/24; G05D 2201/0212; G05D 1/0088
See application file for complete search history.

(56) References Cited

U.S. PATENT DOCUMENTS

| | | | |
|---|---|---|---|
| 2,903,734 A | 9/1959 | Inman | |
| 4,467,706 A | 8/1984 | Batcheller et al. | |
| 4,658,469 A | 4/1987 | Hawkins | |
| 4,997,139 A | 3/1991 | Menard | |
| 7,175,807 B1 | 2/2007 | Jones | |
| 7,762,492 B2 | 7/2010 | Muderlak et al. | |
| 9,015,905 B1 | 4/2015 | Chen | |

(Continued)

FOREIGN PATENT DOCUMENTS

| CN | 1461627 A | * 12/2003 | ........... A47K 13/145 |
|---|---|---|---|
| CN | 1481258 | 3/2004 | |

(Continued)

OTHER PUBLICATIONS

"123rf.com, "Photograph of a roll of Kodak Portra 400 the professional 135 negative film on the white background," Aug. 18, 2018), retrieved Oct. 8, 2021 from URL: <https://www.123rf.com/photo_99841304_bangkok-thailand-mar-21-2018-photograph-of-a-roll-of-kodak-portra-400-the-professional-135-negative-.html>, 1 page".

(Continued)

*Primary Examiner* — Donald R Spamer
*Assistant Examiner* — Priscilla Browning
(74) *Attorney, Agent, or Firm* — Fish & Richardson P.C.

(57) ABSTRACT

Among other things, techniques are described for self-cleaning door handles. A door handle for a vehicle includes a housing including a hand grip; a hygienic film that is formed around a portion of a circumference of the hand grip; a plurality of cylindrical rollers rotatably connected to the housing and are configured to rotationally guide the hygienic film along the portion of the circumference of the hand grip; and a light that is configured to emit electromagnetic radiation in an ultraviolent spectrum and configured to irradiate at least one portion of the hygienic film to reduce a quantity of bacteria on the at least one portion of the hygienic film.

20 Claims, 9 Drawing Sheets

(56) References Cited

U.S. PATENT DOCUMENTS

| | | | |
|---|---|---|---|
| 2003/0115836 A1* | 6/2003 | Suzuki | G03B 17/26 |
| | | | 53/435 |
| 2007/0145292 A1 | 6/2007 | Jones | |
| 2009/0145992 A1 | 6/2009 | Lavy | |
| 2014/0137369 A1 | 5/2014 | Street | |
| 2014/0208541 A1 | 7/2014 | Cowburn | |
| 2014/0338153 A1 | 11/2014 | Dopatka et al. | |
| 2019/0076558 A1* | 3/2019 | Zhang-Miske | B60Q 11/005 |
| 2019/0083666 A1* | 3/2019 | Friberg | A61K 36/185 |

FOREIGN PATENT DOCUMENTS

| | | |
|---|---|---|
| CN | 101111449 | 1/2008 |
| CN | 205063534 | 3/2016 |
| CN | 205370121 | 7/2016 |
| CN | 108104622 | 6/2018 |
| CN | 108952317 | 12/2018 |
| CN | 209815464 | 12/2019 |
| CN | 210948047 | 7/2020 |
| CN | 111599050 | 8/2020 |
| CN | 112922451 | 6/2021 |
| DE | 102015014223 | 5/2016 |
| JP | 2003500182 A * | 1/2003 |
| KR | 1998-0041402 | 8/1998 |
| KR | 2020-0077051 | 6/2020 |

OTHER PUBLICATIONS

[No Author Listed], "SAE International: Surface Vehicle Recommended Practice: Taxonomy and Definitions for Terms Related to Driving Automation Systems for On-Road Motor Vehicles," J3016, Sep. 30, 2016, 30 pages.

AMSJ.com [online], "Dust controls—Positive pressure in operator cabins," Oct. 7, 2019, retrieved on Dec. 16, 2020, retrieved from URL <https://www.amsj.com.au/operator-cabins-dust-control-positive-pressure/>, 6 pages.

Laub, "Schoolchildren develop self-cleaning door handles," WirtschaftsWoche, Jun. 18, 2015 retried Jun. 15, 2021 from URL: <https://www.wiwo.de/technologie/green/hygiene-schülerentwickeln-selbstreinigendetuerklinke/13552062.html>, 2 pages.

trtdeutsche.com, "Turkey: invented the smart doorknob," TRT Deutsch, Jul. 20, 2020, retrieved Jun. 14, 2021 from URL: <https://www.trtdeutsch.com/news-turkei/turkei-intelligente-turklinke-erfunden-2294601>, 2 pages.

* cited by examiner

SELF-CLEANING DOOR HANDLE

FIELD OF THE INVENTION

This description relates to self-cleaning door handles.

BACKGROUND

Autonomous vehicles include many high touch surfaces that can be breeding grounds for bacteria, such as door handles. These surfaces, if left uncleaned, promote spreading of germs by the many different passengers that ride in an autonomous vehicle. Manual cleaning of the surfaces can be a tedious and labor intensive process.

DETAILED DESCRIPTION

Figure 1:
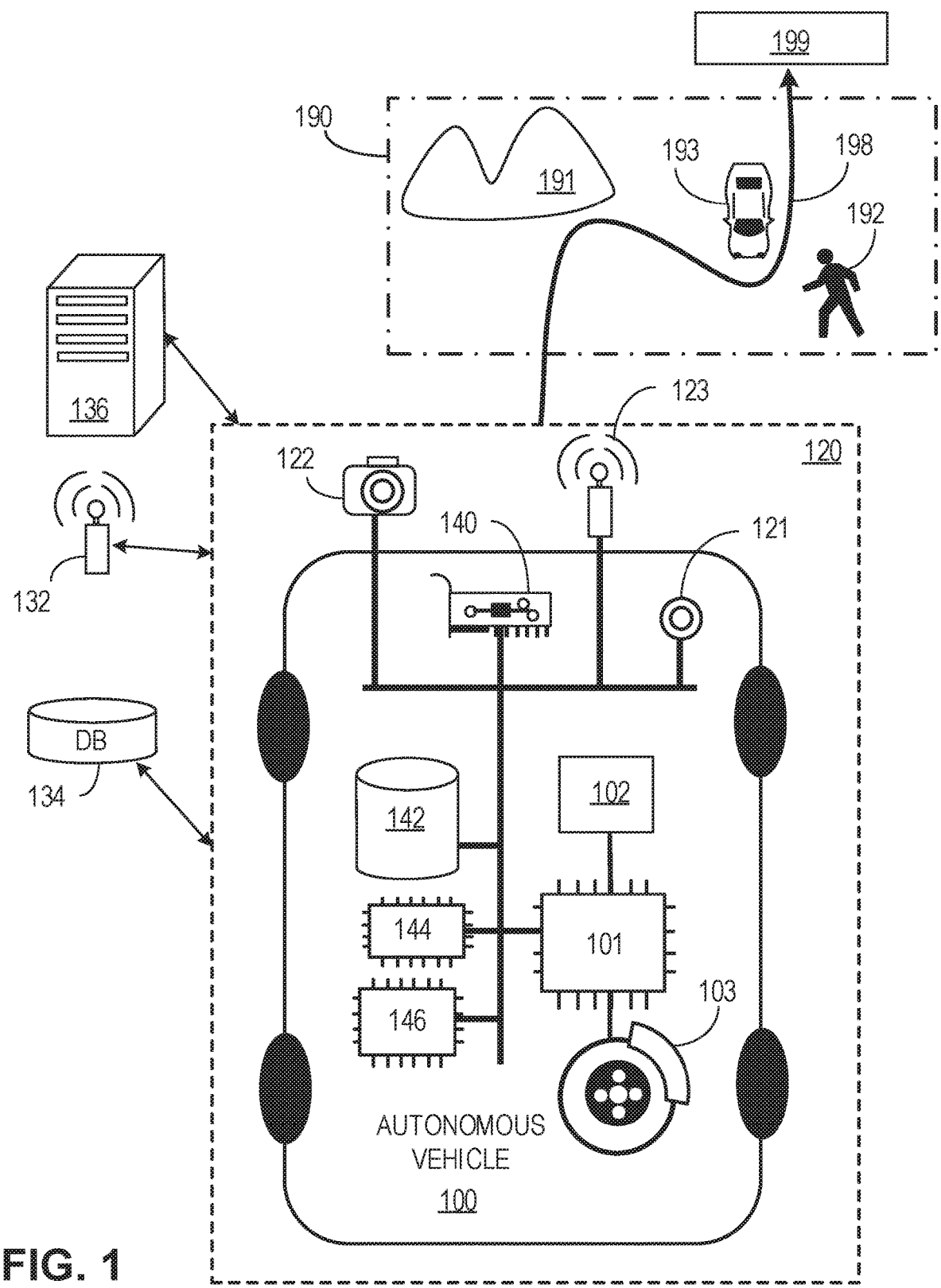
FIG. 1 shows an example of an autonomous vehicle having autonomous capability.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

In the drawings, specific arrangements or orderings of schematic elements, such as those representing devices, modules, instruction blocks and data elements, are shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all embodiments or that the features represented by such element may not be included in or combined with other elements in some embodiments.

Further, in the drawings, where connecting elements, such as solid or dashed lines or arrows, are used to illustrate a connection, relationship, or association between or among two or more other schematic elements, the absence of any such connecting elements is not meant to imply that no connection, relationship, or association can exist. In other words, some connections, relationships, or associations between elements are not shown in the drawings so as not to obscure the disclosure. In addition, for ease of illustration, a single connecting element is used to represent multiple connections, relationships or associations between elements. For example, where a connecting element represents a communication of signals, data, or instructions, it should be understood by those skilled in the art that such element represents one or multiple signal paths (e.g., a bus), as may be needed, to affect the communication.

Reference will now be made in detail to embodiments, examples of which are illustrated in the accompanying drawings. In the following detailed description, numerous specific details are set forth in order to provide a thorough understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

Several features are described hereafter that can each be used independently of one another or with any combination of other features. However, any individual feature may not address any of the problems discussed above or might only address one of the problems discussed above. Some of the problems discussed above might not be fully addressed by any of the features described herein. Although headings are provided, information related to a particular heading, but not found in the section having that heading, may also be found elsewhere in this description. Embodiments are described herein according to the following outline:

1. General Overview
2. System Overview
3. Autonomous Vehicle Architecture
4. Self-Cleaning Door Handles General Overview By detecting when one or more passengers enter and leave the vehicle (e.g., after their ride is complete), a self-cleaning door handle automatically performs a cleaning operation to destroy bacteria on the door handles of the vehicle before a next passenger enters the autonomous vehicle. The self-cleaning door handle can be implemented as an interior and/or exterior door handle and uses either UV light and/or chemical sanitization to destroy the bacteria. The self-cleaning door handle is controllable and uses a sensor network of the autonomous vehicle to know when a passengers' ride is complete and the passenger has left the vehicle. The self-cleaning door handle can be implemented as a continuous roll or as a disposable roll. The self-cleaning door handle is secured in a tamper-resistant housing, so that users cannot tamper or otherwise interfere with the cleaning operation. In some situations, the tamper-resistant housing is hermetically sealed.

Some of the advantages of these techniques include reducing the spread of germs and bacteria such as COVID-19. By implementing a self-cleaning door handle in a tamper-resistant housing, manual cleaning after each ride can be avoided or reduced, thus reducing labor costs for a fleet operator. The self-cleaning door handle also gives passengers peace of mind about their risk of being infected, which can increase utilization of fleet vehicles by the public. The self-cleaning door handle also allows a fleet operator to better comply with government regulations and standards that could arise during, for example, a pandemic.

System Overview

FIG. 1 shows an example of an autonomous vehicle 100 having autonomous capability.

As used herein, the term "autonomous capability" refers to a function, feature, or facility that enables a vehicle to be partially or fully operated without real-time human intervention, including without limitation fully autonomous vehicles, highly autonomous vehicles, and conditionally autonomous vehicles.

As used herein, an autonomous vehicle (AV) is a vehicle that possesses autonomous capability.

As used herein, "vehicle" includes means of transportation of goods or people. For example, cars, buses, trains, airplanes, drones, trucks, boats, ships, submersibles, dirigibles, etc. A driverless car is an example of a vehicle.

As used herein, "trajectory" refers to a path or route to navigate an AV from a first spatiotemporal location to second spatiotemporal location. In an embodiment, the first spatiotemporal location is referred to as the initial or starting location and the second spatiotemporal location is referred to as the destination, final location, goal, goal position, or goal location. In some examples, a trajectory is made up of one or more segments (e.g., sections of road) and each segment is made up of one or more blocks (e.g., portions of a lane or intersection). In an embodiment, the spatiotemporal locations correspond to real world locations. For example, the spatiotemporal locations are pick up or drop-off locations to pick up or drop-off persons or goods.

As used herein, "sensor(s)" includes one or more hardware components that detect information about the environment surrounding the sensor. Some of the hardware components can include sensing components (e.g., image sensors, biometric sensors), transmitting and/or receiving components (e.g., laser or radio frequency wave transmitters and receivers), electronic components such as analog-to-digital converters, a data storage device (such as a RAM and/or a nonvolatile storage), software or firmware components and data processing components such as an ASIC (application-specific integrated circuit), a microprocessor and/or a microcontroller.

As used herein, a "scene description" is a data structure (e.g., list) or data stream that includes one or more classified or labeled objects detected by one or more sensors on the AV vehicle or provided by a source external to the AV.

As used herein, a "road" is a physical area that can be traversed by a vehicle, and may correspond to a named thoroughfare (e.g., city street, interstate freeway, etc.) or may correspond to an unnamed thoroughfare (e.g., a driveway in a house or office building, a section of a parking lot, a section of a vacant lot, a dirt path in a rural area, etc.). Because some vehicles (e.g., 4-wheel-drive pickup trucks, sport utility vehicles, etc.) are capable of traversing a variety of physical areas not specifically adapted for vehicle travel, a "road" may be a physical area not formally defined as a thoroughfare by any municipality or other governmental or administrative body.

As used herein, a "lane" is a portion of a road that can be traversed by a vehicle. A lane is sometimes identified based on lane markings. For example, a lane may correspond to most or all of the space between lane markings, or may correspond to only some (e.g., less than 50%) of the space between lane markings. For example, a road having lane markings spaced far apart might accommodate two or more vehicles between the markings, such that one vehicle can pass the other without traversing the lane markings, and thus could be interpreted as having a lane narrower than the space between the lane markings, or having two lanes between the lane markings. A lane could also be interpreted in the absence of lane markings. For example, a lane may be defined based on physical features of an environment, e.g., rocks and trees along a thoroughfare in a rural area or, e.g., natural obstructions to be avoided in an undeveloped area. A lane could also be interpreted independent of lane markings or physical features. For example, a lane could be interpreted based on an arbitrary path free of obstructions in an area that otherwise lacks features that would be interpreted as lane boundaries. In an example scenario, an AV could interpret a lane through an obstruction-free portion of a field or empty lot. In another example scenario, an AV could interpret a lane through a wide (e.g., wide enough for two or more lanes) road that does not have lane markings. In this scenario, the AV could communicate information about the lane to other AVs so that the other AVs can use the same lane information to coordinate path planning among themselves.

"One or more" includes a function being performed by one element, a function being performed by more than one element, e.g., in a distributed fashion, several functions being performed by one element, several functions being performed by several elements, or any combination of the above.

It will also be understood that, although the terms first, second, etc. are, in some instances, used herein to describe various elements, these elements should not be limited by these terms. These terms are only used to distinguish one element from another. For example, a first contact could be termed a second contact, and, similarly, a second contact could be termed a first contact, without departing from the scope of the various described embodiments. The first contact and the second contact are both contacts, but they are not the same contact.

The terminology used in the description of the various described embodiments herein is for the purpose of describing particular embodiments only and is not intended to be limiting. As used in the description of the various described embodiments and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this description, specify the presence of stated features, integers, steps, operations, elements, and/or components, but do not preclude the presence or addition of one or more other features, integers, steps, operations, elements, components, and/or groups thereof.

As used herein, the term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

As used herein, an AV system refers to the AV along with the array of hardware, software, stored data, and data generated in real-time that supports the operation of the AV. In an embodiment, the AV system is incorporated within the AV. In an embodiment, the AV system is spread across several locations. For example, some of the software of the AV system is implemented on a cloud computing environment similar to a cloud computing environment.

In general, this document describes technologies applicable to any vehicles that have one or more autonomous capabilities including fully autonomous vehicles, highly autonomous vehicles, and conditionally autonomous vehicles, such as so-called Level 5, Level 4 and Level 3 vehicles, respectively (see SAE International's standard J3016: Taxonomy and Definitions for Terms Related to On-Road Motor Vehicle Automated Driving Systems, which is incorporated by reference in its entirety, for more details on the classification of levels of autonomy in vehicles). The technologies described in this document are also applicable to partially autonomous vehicles and driver assisted vehicles, such as so-called Level 2 and Level 1 vehicles (see SAE International's standard J3016: Taxonomy and Definitions for Terms Related to On-Road Motor Vehicle Automated Driving Systems). In an embodiment, one or more of the Level 1, 2, 3, 4 and 5 vehicle systems may automate certain vehicle operations (e.g., steering, braking, and using maps) under certain operating conditions based on processing of sensor inputs. The technologies described in this document can benefit vehicles in any levels, ranging from fully autonomous vehicles to human-operated vehicles.

Autonomous vehicles have advantages over vehicles that require a human driver. One advantage is safety. For example, in 2016, the United States experienced 6 million automobile accidents, 2.4 million injuries, 40,000 fatalities, and 13 million vehicles in crashes, estimated at a societal cost of $910+ billion. U.S. traffic fatalities per 100 million miles traveled have been reduced from about six to about one from 1965 to 2015, in part due to additional safety measures deployed in vehicles. For example, an additional half second of warning that a crash is about to occur is believed to mitigate 60% of front-to-rear crashes. However, passive safety features (e.g., seat belts, airbags) have likely reached their limit in improving this number. Thus, active safety measures, such as automated control of a vehicle, are the likely next step in improving these statistics. Because human drivers are believed to be responsible for a critical pre-crash event in 95% of crashes, automated driving systems are likely to achieve better safety outcomes, e.g., by reliably recognizing and avoiding critical situations better than humans; making better decisions, obeying traffic laws, and predicting future events better than humans; and reliably controlling a vehicle better than a human.

Referring to FIG. 1, an AV system 120 operates the AV 100 along a trajectory 198 through an environment 190 to a destination 199 (sometimes referred to as a final location) while avoiding objects (e.g., natural obstructions 191, vehicles 193, pedestrians 192, cyclists, and other obstacles) and obeying rules of the road (e.g., rules of operation or driving preferences).

In an embodiment, the AV system 120 includes devices 101 that are instrumented to receive and act on operational commands from the computer processors 146. We use the term "operational command" to mean an executable instruction (or set of instructions) that causes a vehicle to perform an action (e.g., a driving maneuver). Operational commands can, without limitation, including instructions for a vehicle to start moving forward, stop moving forward, start moving backward, stop moving backward, accelerate, decelerate, perform a left turn, and perform a right turn. Examples of devices 101 include a steering control 102, brakes 103, gears, accelerator pedal or other acceleration control mechanisms, windshield wipers, side-door locks, window controls, and turn-indicators.

In an embodiment, the AV system 120 includes sensors 121 for measuring or inferring properties of state or condition of the AV 100, such as the AV's position, linear and angular velocity and acceleration, and heading (e.g., an orientation of the leading end of AV 100). Example of sensors 121 are GPS, inertial measurement units (IMU) that measure both vehicle linear accelerations and angular rates, wheel speed sensors for measuring or estimating wheel slip ratios, wheel brake pressure or braking torque sensors, engine torque or wheel torque sensors, and steering angle and angular rate sensors.

In an embodiment, the sensors 121 also include sensors for sensing or measuring properties of the AV's environment. For example, monocular or stereo video cameras 122 in the visible light, infrared or thermal (or both) spectra, LiDAR 123, RADAR, ultrasonic sensors, time-of-flight (TOF) depth sensors, speed sensors, temperature sensors, humidity sensors, and precipitation sensors.

In an embodiment, the sensors 121 also include sensors for sensing or measuring properties of the AV's interior cabin. For example, monocular or stereo video cameras in the visible light, infrared or thermal (or both) spectra detect when a passenger is present within the AV 100. In an embodiment, the sensors 121 also include seat weight sensors for sensing whether a passenger is sitting in a seat and door sensors for sensing whether a particular door of the AV 100 is open.

In an embodiment, the AV system 120 includes a data storage unit 142 and memory 144 for storing machine instructions associated with computer processors 146 or data collected by sensors 121. In an embodiment, the data storage unit 142 and memory 144 store historical, real-time, and/or predictive information about the environment 190. In an embodiment, the stored information includes maps, driving performance, traffic congestion updates or weather conditions. In an embodiment, data relating to the environment 190 is transmitted to the AV 100 via a communications channel from a remotely located database 134.

In an embodiment, the AV system 120 includes communications devices 140 for communicating measured or inferred properties of other vehicles' states and conditions, such as positions, linear and angular velocities, linear and angular accelerations, and linear and angular headings to the AV 100. These devices include Vehicle-to-Vehicle (V2V) and Vehicle-to-Infrastructure (V2I) communication devices and devices for wireless communications over point-to-point or ad hoc networks or both. In an embodiment, the communications devices 140 communicate across the electromagnetic spectrum (including radio and optical communications) or other media (e.g., air and acoustic media). A combination of Vehicle-to-Vehicle (V2V) Vehicle-to-Infrastructure (V2I) communication (and, in some embodiments, one or more other types of communication) is sometimes referred to as Vehicle-to-Everything (V2X) communication. V2X communication typically conforms to one or more communications standards for communication with, between, and among autonomous vehicles.

In an embodiment, the communication devices 140 include communication interfaces. For example, wired, wireless, WiMAX, WiFi, Bluetooth, satellite, cellular, optical, near field, infrared, or radio interfaces. The communication interfaces transmit data from a remotely located database 134 to AV system 120. In an embodiment, the remotely located database 134 is embedded in a cloud computing environment. The communication interfaces 140 transmit data collected from sensors 121 or other data related to the operation of AV 100 to the remotely located database 134. In an embodiment, communication interfaces 140 transmit information that relates to teleoperations to the AV 100. In some embodiments, the AV 100 communicates with other remote (e.g., "cloud") servers 136.

In an embodiment, the remotely located database 134 also stores and transmits digital data (e.g., storing data such as road and street locations). Such data is stored on the memory 144 on the AV 100, or transmitted to the AV 100 via a communications channel from the remotely located database 134.

In an embodiment, the remotely located database 134 stores and transmits historical information about driving properties (e.g., speed and acceleration profiles) of vehicles that have previously traveled along trajectory 198 at similar times of day. In one implementation, such data may be stored on the memory 144 on the AV 100, or transmitted to the AV 100 via a communications channel from the remotely located database 134.

Computing devices 146 located on the AV 100 algorithmically generate control actions based on both real-time sensor data and prior information, allowing the AV system 120 to execute its autonomous driving capabilities.

In an embodiment, the AV system 120 includes computer peripherals 132 coupled to computing devices 146 for providing information and alerts to, and receiving input from, a user (e.g., an occupant or a remote user) of the AV 100. The coupling is wireless or wired. Any two or more of the interface devices may be integrated into a single device.

In an embodiment, the AV system 120 receives and enforces a privacy level of a passenger, e.g., specified by the passenger or stored in a profile associated with the passenger. The privacy level of the passenger determines how particular information associated with the passenger (e.g., passenger comfort data, biometric data, etc.) is permitted to be used, stored in the passenger profile, and/or stored on the cloud server 136 and associated with the passenger profile. In an embodiment, the privacy level specifies particular information associated with a passenger that is deleted once the ride is completed. In an embodiment, the privacy level specifies particular information associated with a passenger and identifies one or more entities that are authorized to access the information. Examples of specified entities that are authorized to access information can include other AVs, third party AV systems, or any entity that could potentially access the information.

A privacy level of a passenger can be specified at one or more levels of granularity. In an embodiment, a privacy level identifies specific information to be stored or shared. In an embodiment, the privacy level applies to all the information associated with the passenger such that the passenger can specify that none of her personal information is stored or shared. Specification of the entities that are permitted to access particular information can also be specified at various levels of granularity. Various sets of entities that are permitted to access particular information can include, for example, other AVs, cloud servers 136, specific third party AV systems, etc.

In an embodiment, the AV system 120 or the cloud server 136 determines if certain information associated with a passenger can be accessed by the AV 100 or another entity. For example, a third-party AV system that attempts to access passenger input related to a particular spatiotemporal location must obtain authorization, e.g., from the AV system 120 or the cloud server 136, to access the information associated with the passenger. For example, the AV system 120 uses the passenger's specified privacy level to determine whether the passenger input related to the spatiotemporal location can be presented to the third-party AV system, the AV 100, or to another AV. This enables the passenger's privacy level to specify which other entities are allowed to receive data about the passenger's actions or other data associated with the passenger.

Autonomous Vehicle Architecture

Figure 2:
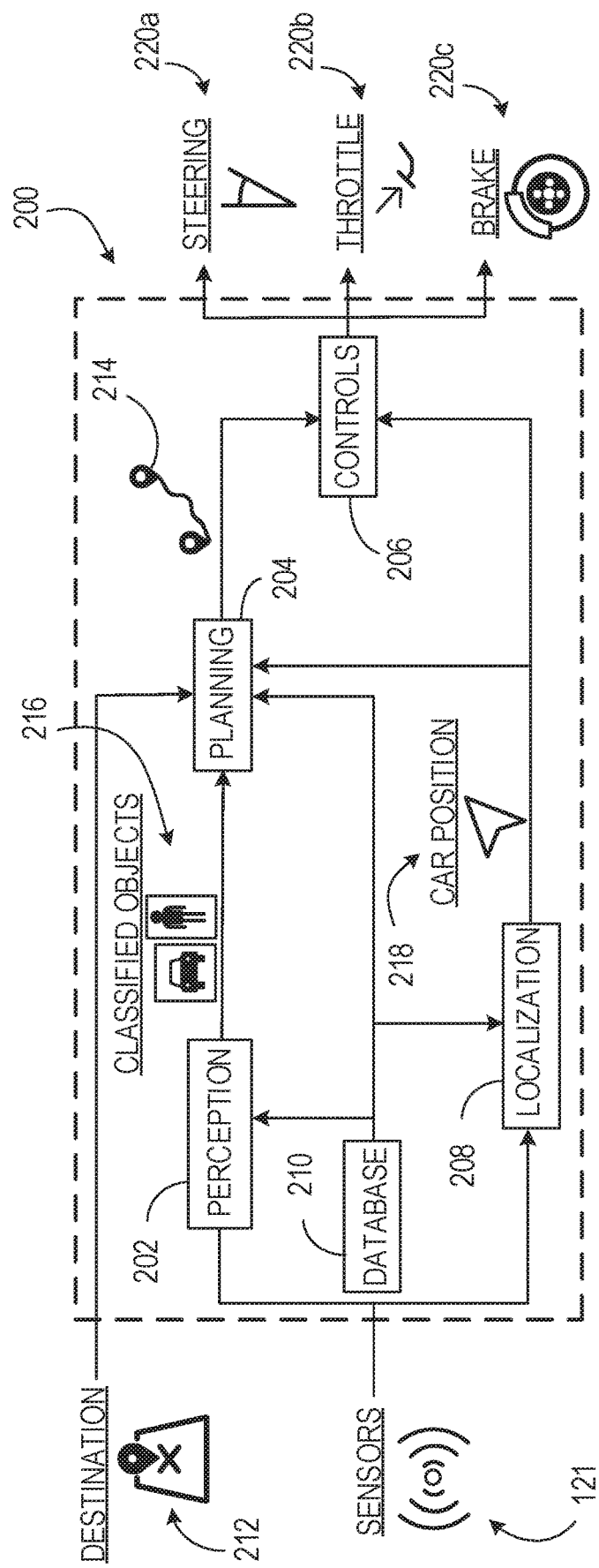
FIG. 2 shows an example architecture for an autonomous vehicle.

FIG. 2 shows an example architecture 200 for an autonomous vehicle (e.g., the AV 100 shown in FIG. 1). The architecture 200 includes a perception module 202 (sometimes referred to as a perception circuit), a planning module 204 (sometimes referred to as a planning circuit), a control module 206 (sometimes referred to as a control circuit), a localization module 208 (sometimes referred to as a localization circuit), and a database module 210 (sometimes referred to as a database circuit). Each module plays a role in the operation of the AV 100. Together, the modules 202, 204, 206, 208, and 210 may be part of the AV system 120 shown in FIG. 1. In some embodiments, any of the modules 202, 204, 206, 208, and 210 is a combination of computer software (e.g., executable code stored on a computer-readable medium) and computer hardware (e.g., one or more microprocessors, microcontrollers, application-specific integrated circuits [ASICs]), hardware memory devices, other types of integrated circuits, other types of computer hardware, or a combination of any or all of these things). Each of the modules 202, 204, 206, 208, and 210 is sometimes referred to as a processing circuit (e.g., computer hardware, computer software, or a combination of the two). A combination of any or all of the modules 202, 204, 206, 208, and 210 is also an example of a processing circuit.

In use, the planning module 204 receives data representing a destination 212 and determines data representing a trajectory 214 (sometimes referred to as a route) that can be traveled by the AV 100 to reach (e.g., arrive at) the destination 212. In order for the planning module 204 to determine the data representing the trajectory 214, the planning module 204 receives data from the perception module 202, the localization module 208, and the database module 210.

The perception module 202 identifies nearby physical objects using one or more sensors 121, e.g., as also shown in FIG. 1. The objects are classified (e.g., grouped into types such as pedestrian, bicycle, automobile, traffic sign, etc.) and a scene description including the classified objects 216 is provided to the planning module 204.

The planning module 204 also receives data representing the AV position 218 from the localization module 208. The localization module 208 determines the AV position by using data from the sensors 121 and data from the database module 210 (e.g., a geographic data) to calculate a position. For example, the localization module 208 uses data from a GNSS (Global Navigation Satellite System) sensor and geographic data to calculate a longitude and latitude of the AV. In an embodiment, data used by the localization module 208 includes high-precision maps of the roadway geometric properties, maps describing road network connectivity properties, maps describing roadway physical properties (such as traffic speed, traffic volume, the number of vehicular and cyclist traffic lanes, lane width, lane traffic directions, or lane marker types and locations, or combinations of them), and maps describing the spatial locations of road features such as crosswalks, traffic signs or other travel signals of various types. In an embodiment, the high-precision maps are constructed by adding data through automatic or manual annotation to low-precision maps.

The control module 206 receives the data representing the trajectory 214 and the data representing the AV position 218 and operates the control functions 220a-c (e.g., steering, throttling, braking, ignition) of the AV in a manner that will cause the AV 100 to travel the trajectory 214 to the destination 212. For example, if the trajectory 214 includes a left turn, the control module 206 will operate the control functions 220a-c in a manner such that the steering angle of the steering function will cause the AV 100 to turn left and the throttling and braking will cause the AV 100 to pause and wait for passing pedestrians or vehicles before the turn is made.

Self-Cleaning Door Handles

Figure 3:
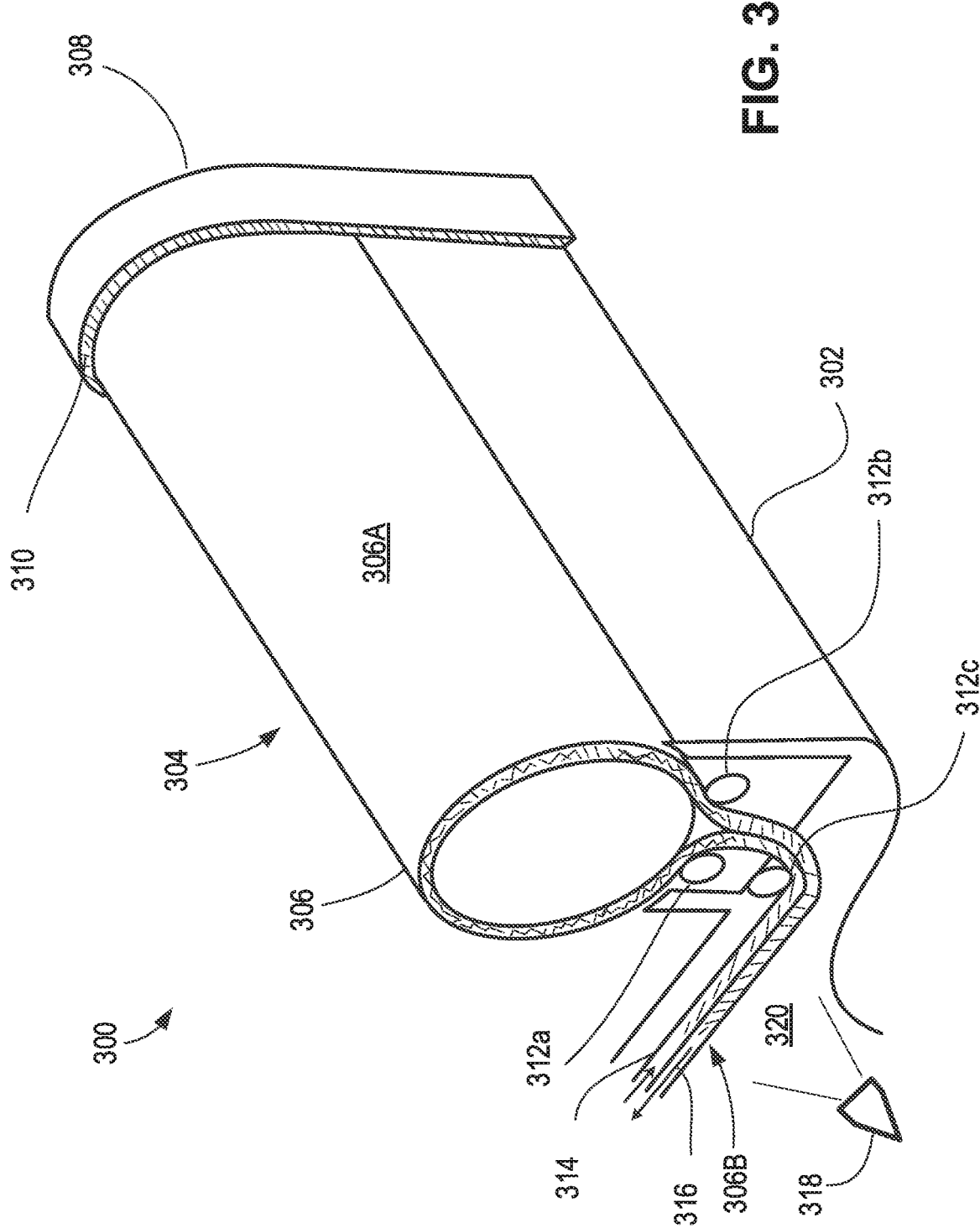
FIG. 3 shows a cross section of a self-cleaning door handle for a vehicle with a cylindrical hand grip.

FIG. 3 shows a cross section of a self-cleaning (or self-sanitizing) door handle 300 for a vehicle (such as AV 100 shown in FIG. 1). The self-cleaning door handle 300 is mounted to or inside a door of a vehicle and can be adapted to be used as an interior door handle or an exterior door handle, or both interior and exterior door handles, which can be installed as a single assembly in each passenger door. The self-cleaning door handle 300 includes a tamper-resistant housing 302 that is rigidly connected to the door and provides a supporting structure for containing the parts of the self-cleaning door handle. In some embodiments, the housing 302 is fabricated using injection molded plastic but can be made out of other rigid or structurally stiff materials, such as metal or composites.

The housing 302 includes a rigid hand grip 304. In some embodiments, the hand grip 304 is cylindrical, however, any shape that facilitates the movement of film as described further below, can be used. The hand grip 304 is configured as a guiding surface for a hygienic film 306. The hand grip 304 has a smooth outer diametrical surface to accommodate sliding of the hygienic film 306. The hand grip 304 of the door handle 300 (and the hygienic film 306 that is wrapped and guided around the hand grip 304) is configured as a gripping surface that a passenger can grip onto for opening and closing the door.

In some embodiments, the hand grip 304 is fixedly attached to the housing 302 using a pair of end caps 308. In some embodiments, the end caps 308 fixedly attached the door handle 304 to the vehicle door in addition to, or instead of, the housing 302. In this way, the end caps 308 can be integrated into the vehicle door itself. This can provide aesthetic advantages.

In some embodiments, the door handle can include more than one handle. For example, as will be described with reference to FIG. 6, one handle can be mounted on an interior of the door and one self-cleaning handle can be mounted on the outside of the door. In this case, the hygienic film traverses through the door from one side to the other and passes through a cleaning chamber for cleaning.

In some embodiments, the hand grip 304 is about 10 cm in length and about 2-3 cm in diameter, but other dimensions and aspect ratios can be used depending on design choice.

The hygienic film 306 covers an exposed surface portion of the hand grip 304 that the passenger touches when opening or closing the door. Once the ride is complete and one or more sensors detect that the passenger has exited the vehicle, the hygienic film 306 is moved into a cleaning chamber 320 where it is cleaned (or "refreshed") by exposure to UV light and/or disinfectant agents before the next passenger enters the vehicle. The cleaning chamber 320 is internal to the housing 302 and allows hygienic film 306 to traverse through.

In some embodiments, a light indicator (e.g., a green LED) disposed on the housing 302 or inside or outside the vehicle alerts the passengers inside or outside the vehicle that the cleaning process has completed. In some implementations, if the door handle system fails or the hygienic film 306 is depleted or disinfectant agents are depleted, the door handle system communicates these conditions to the vehicle processor and/or a network-based fleet computer, so that the vehicle can be taken "off line" for maintenance. In some embodiments, the doors of the vehicle are automatically locked until the cleaning has completed.

In some embodiments, the hygienic film 306 is a plastic film of 0.1-1 mm thickness and is malleable such that it is can be contoured around a circumference of the hand grip 304 of the housing 302. In some embodiments, the hygienic film 306 is hygienic paper (e.g., tissue paper, toilet paper, etc.). In some embodiments, the hygienic film 306 is hygienic rubber (e.g., nitrile rubber, latex rubber, etc.). However, various thicknesses and hygienic materials can be used depending on design choice.

The end caps 308 are installed at opposite ends of the hand grip 304. For clarify, one end cap 308 is show in FIG. 3. The end caps conceals the edges of the hygienic film 306 and prevents the edges of the hygienic film 306 from being caught or snagged during rotation around the hand grip 304. In some embodiments, the end caps 308 cover an entire edge of the hygienic film 306. In some embodiments, the tamper-resistant housing 302 is also hermetically sealed so that air from within an interior of the vehicle cannot contaminate new or sanitized hygienic film 306. For example, in some embodiments, a rubber grommet is used on each side of the tamper-resistant housing 302 to seal around the hygienic film. In some embodiments, an active door or hatch with a door seal (e.g., a seal around the perimeter of the door that compresses against the tamper-resistant housing 302 to hermetically seal the tamper-resistant housing 302) is closed when passengers are present within the vehicle to avoid tempering. In some embodiments, the door or hatch is openable by a technician for servicing. The end caps 308 include a recess 310 for accommodating the hygienic film 306 so that the hygienic film 306 cannot be removed from the self-cleaning door handle 300 when both end caps 308 are installed.

As shown in FIG. 3, the hygienic film 306 is wrapped around a portion of the outer diametrical surface of the hand grip 304. A first portion 306A of the hygienic film 306 is accessible to the passenger and can be touched. A second portion 306B of the hygienic film 306 is not accessible to the passenger and cannot be touched. The first portion 306 of the hygienic film 306 covers approximately 270 degrees around the circumference of the hand grip 304. The remaining 90 degrees of the hygienic film 306 is within the housing 302 and is part of the second portion 306B.

A set of rollers 312a-312c guide the hygienic film 306 from a source 314 to a destination 316, such as a cleaning chamber or waste repository for sanitizing film or storing shredded film, respectively. In some embodiments, at least one of the set of rollers 312a-312c is a plurality of cylindrical rollers rotatably connected to the housing and are configured to guide the hygienic film along the portion of the circumference of the hand grip 304. In some embodiments, at least one of the set of rollers 312a-312c is a drive roller that is mechanically coupled to a motor shaft, which is electrically connected to a microcontroller, as described in reference to FIG. 9.

In some embodiments, the drive roller is not needed and instead the hand grip 304 rotates with respect to the housing 302 to advance the hygienic film 306. In this case, instead of having a smooth outer surface, the hand grip 304 has an outer surface with a frictional engagement with the hygienic film 306 such that upon rotation of the hand grip by a motor rotatable connected to the hand grip 304, the hygienic film 306 advances. In this case, the hand grip 304 is configured as a roller for advancing the hygienic film 306.

In some embodiments, the cylindrical rollers 312a-312c or the hand grip 304 are configured to advance the hygienic film 306 in response to a vehicle processor determining that a passenger's ride has concluded and that the passengers have exited the vehicle. For example, when the vehicle processor detects that all passengers have left the vehicle (e.g., using sensors 121) it can instruct the microcomputer (e.g., through a CAN bus) to replace the used (or potentially contaminated) hygienic film 306 with a new, sanitized, hygienic film 306. In this way, the hygienic film 306 is "refreshed" so that subsequent passengers of the vehicle will not have to touch a door handle that a previous passenger has already touched.

For example, the vehicle processor may have knowledge of the route the vehicle takes and knows when the ride is complete. Once the vehicle processor determines that the ride is complete, an occupancy sensor (e.g., sensors 121) of the vehicle generates an occupancy signal that represents whether passengers are still present within the vehicle. The occupancy sensors can include motion sensors, heat sensors, cameras, seat pressure sensors or any other sensor capable of detecting passengers in the vehicle. The vehicle processor receives the occupancy signal and waits until all passengers have exited the vehicle. In some embodiments, a separate occupancy signal is generated for each seat of the vehicle. In some embodiments, a door sensor associated with each door of the vehicle generates a door status signal that indicates whether the doors are open or closed. These additional door status signals provide a confirmation (or second independent measurement) that the passenger has exited the vehicle at ride conclusion.

In some embodiments, knowledge of how many passengers were present during a ride and where they were sitting (e.g., an electronic manifest) are used to determine whether passengers have entered or exited the vehicle. For example, if only one passenger was detected during a ride, the vehicle may determine that only the door handle where the passenger was sitting needs to be sanitized. If, on the other hand, each seat of the vehicle was occupied then the vehicle may determine to sanitize all the door handles of the vehicle.

All hygienic film 306 that is exposed to the possibility of touching by the passenger is refreshed after the passengers have exited the vehicle. In the embodiment where the first portion 306A of the hygienic film 306 covers approximately 270 degrees around the circumference of the hand grip 304, this means that the set of rollers 312a-312c will guide via the action of the driver roller to advance the hygienic film 306, so that all exposed hygienic film 306 (e.g., portion 306A) is advanced at least 270 degrees around the circumference of the hand grip 304 so that a clean supply of hygienic film 306 completely replaces the exposed hygienic film 306 (i.e., the exposed hygienic film 306 is "refreshed").

Other than the drive roller that is controlled by the vehicle processor, the other rollers of the set of rollers 312a-312c are free spinning or fixed rollers (e.g., film guide posts) to guide and keep the hygienic film 306 in place and taught. In some embodiments, the rollers 312a-312c are cylindrical and span the entire length of the door handle 300 (i.e., from one end cap 300 to the opposite end cap). In an embodiment, the rollers 312a-312c are mounted to the end caps 310 or the housing 302, depending on placement within the door handle 300. In some embodiments, the rollers 312a-312c are rubber coated for a frictional engagement with the hygienic film 306. In some embodiments, rollers are installed in pairs, i.e., on opposites sides of the hygienic film 306, to squeeze the hygienic film 306 for an improved frictional engagement.

As will be explained with reference to specific embodiments below, some embodiments of the hygienic film 306 are a closed loop, where the hygienic film 306 is used by a vehicle, cleaned by a sanitization source 318 within the door handle 300, and reused by the vehicle. In some embodiments, the hygienic film 306 is retrieved from a source repository, sanitized if needed, used by the vehicle, and deposited into a waste repository after use. In some embodiments, the sanitization source 388 is mounted within the housing 302 of the door handle 300.

The sanitization source 318 is implemented as a source of ultraviolet (UV) irradiation (or simply UV light 318) that is configured to destroy bacteria or reduce a quantity of bacteria on at least one portion of a surface of the hygienic film 306. In some embodiments, the sanitization source is a disinfectant agent that is sprayed onto the surface of hygienic film 306. Either the UV light 318 or the sprayed agent may be used in any of the embodiments described in this specification. The UV light 318 is mounted within the housing 302 of the door handle 300 and is not accessible by a passenger of the vehicle (i.e., interference by a passenger is reduced). The sanitization source 318 can be located within the cleaning chamber 320.

In some embodiments, the UV light 318 eliminates most, but not all, bacteria. A quantity of bacteria is reduced by the UV light 318. In some embodiments, a sanitation or disinfectant agent is used in addition to, or in lieu of, a UV light. In some embodiments, heat can also be applied to reduce bacteria and could be used in combination with a disinfectant agent and/or UV light).

In some embodiments, the UV light 318 of the door handle is configured to irradiate the at least one portion of the hygienic film upon being guided away from the hand grip by the plurality of cylindrical rollers. The light is mounted within the housing in a cleaning chamber where it is able to sanitize the hygienic after use. When the rollers advance the hygienic film away from the hand grip, the contaminated portion of the hygienic film moves in the optical path of the light and is sanitized.

In the case of UV light 318, a wavelength range of 240-280 nm is used to disinfect the surface of the hygienic film 306 that is in the optical path of the UV light 318. For example, when the first portion 306A of the hygienic film 306 advances to a location in the optical path of the UV light 318 (i.e., in front of the UV light 318), the UV light 318 irradiates the hygienic film 306 with UV light within a wavelength range of 240-280 nm to disinfect the surface of the hygienic film 306 so that it can be reused.

The UV light 318 is controlled by the vehicle processor to be in an "on" state or an "off" state. For example, there is usually no need for the UV light 318 to be "on" while the vehicle is in motion and traversing to its destination. Typically, the UV light 318 will be "on" when the hygienic film 306 is cleaned after the passengers ride as completed and the passenger has left the vehicle. However, in some embodiments, the passenger may manually request that the hygienic film 306 be cleaned, which can trigger the vehicle processor to advance the hygienic film 306 and turn on the UV light 318. The manual request to clean the door handle can be a speech command spoken by the passenger, which is interpreted by a speech recognition engine implemented by the vehicle processor.

In some embodiments, the cylindrical rollers 312a-312c of the door handle 300 are configured to advance the hygienic film 306 such that a contaminated portion of the hygienic film is retracted within the housing 302 and irradiated by ultraviolet radiation from the UV light 318 to reduce the quantity of bacteria on a contaminated portion of the hygienic film 306.

The rollers 312a-312c are controlled by the vehicle processor to advance when the passenger has exited the vehicle or when a touch/gesture sensor is activated. For example, even when the passenger is in the vehicle, the passenger may wish to advance the hygienic film. When the rollers 312a-312c advance the hygienic film, the contaminated portion is retracted within the cleaning chamber in the housing for sanitization. For example, the passenger can use a GUI of a computer within the vehicle or via an app of their mobile device (e.g., smartphone, wearable computer, tablet computer) to request all self-cleaning door handles be cleaned within the vehicle. This can increase a passenger's confidence that the vehicle is clean and sanitized. In some embodiments, a speech command spoken by the passenger can be used to initiate cleaning of the door handles. For example, a speech recognition engine implemented by the vehicle processor can be used to recognize the speech command and initiate a cleaning cycle.

Figure 4:
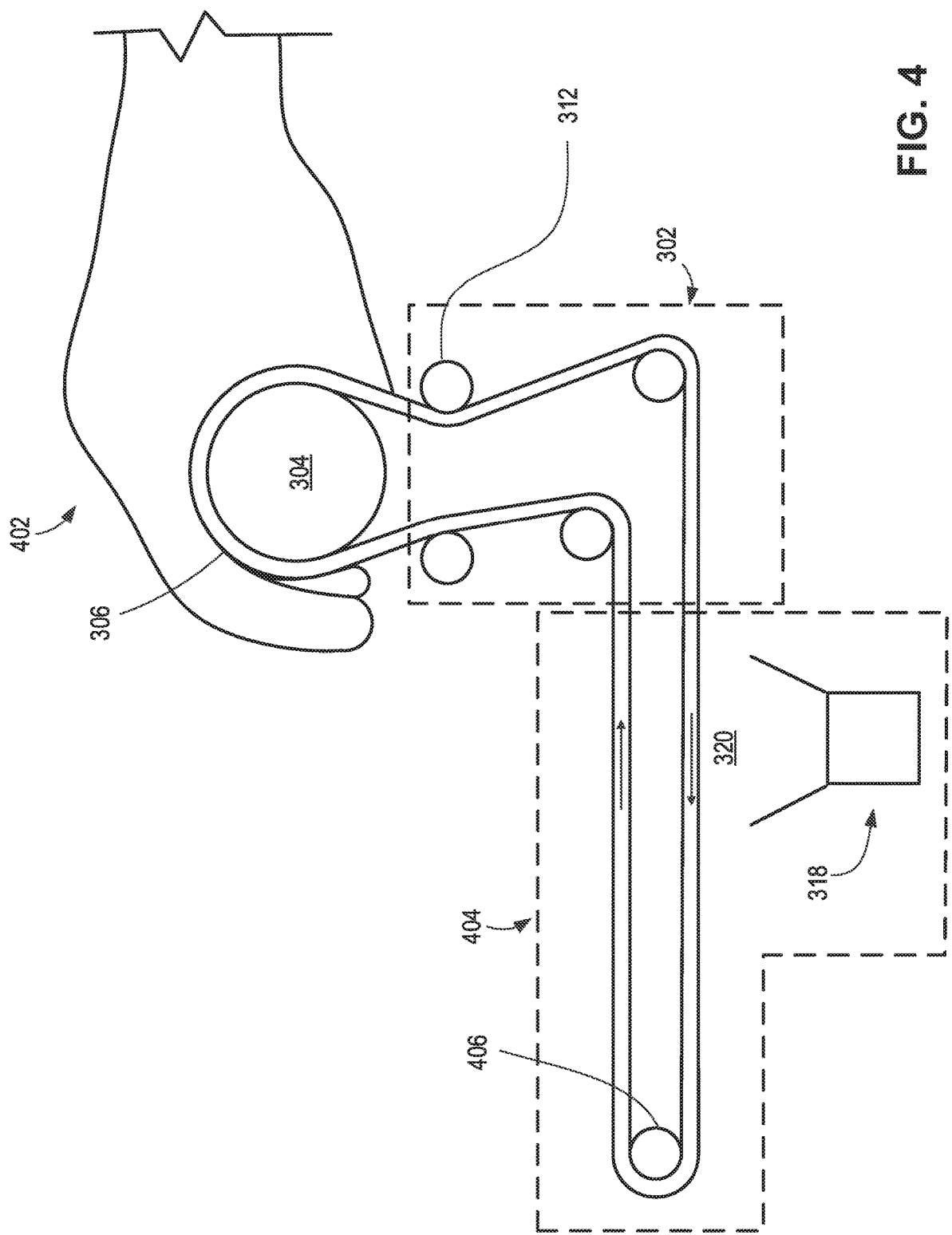
FIG. 4 shows a schematic of a self-cleaning door handle for a vehicle that includes a continuous roll hygienic film.

FIG. 4 shows a passenger 402 grabbing the hygienic film 306 that is wrapped around the rigid hand grip 304. When the passenger 402 pushes or pulls their hand, force is applied to the rigid hand grip 304, to the housing 302 (schematically shown as region 302) and ultimately to the door 404 (schematically shown as region 404) of the vehicle. The embodiment shown is a first embodiment where the hygienic film 306 is implemented as a closed continuous loop (i.e., a closed roll) with or without a seam. In this case, the hygienic film 306 is reused. For example, a contaminated portion of the hygienic film 306 is advanced by the rollers 312a-312c and sanitized after the passenger has exited, but then advanced back to the hand grip 304 for the next passenger.

The continuous loop of the hygienic film 306 is achieved by a roller 406 that reverses the direction of the hygienic film 306 during the cleaning process. In operation, the hygienic film 306 is guided by the rollers in the direction of the arrows shown in FIG. 4. Once hygienic film 306 is sanitized in the cleaning chamber by the UV light 318, the direction of the hygienic film 306 is reversed by roller 406 and is guided to the hand grip to be reused.

In this embodiment, the UV light 318, at least one roller, and a portion of the hygienic film 306 is housed within the door 404. In these cases, it can be advantageous to integrate at least some of these components into the door structure itself 404 to minimize space needed for the self-cleaning operations.

Figure 5:
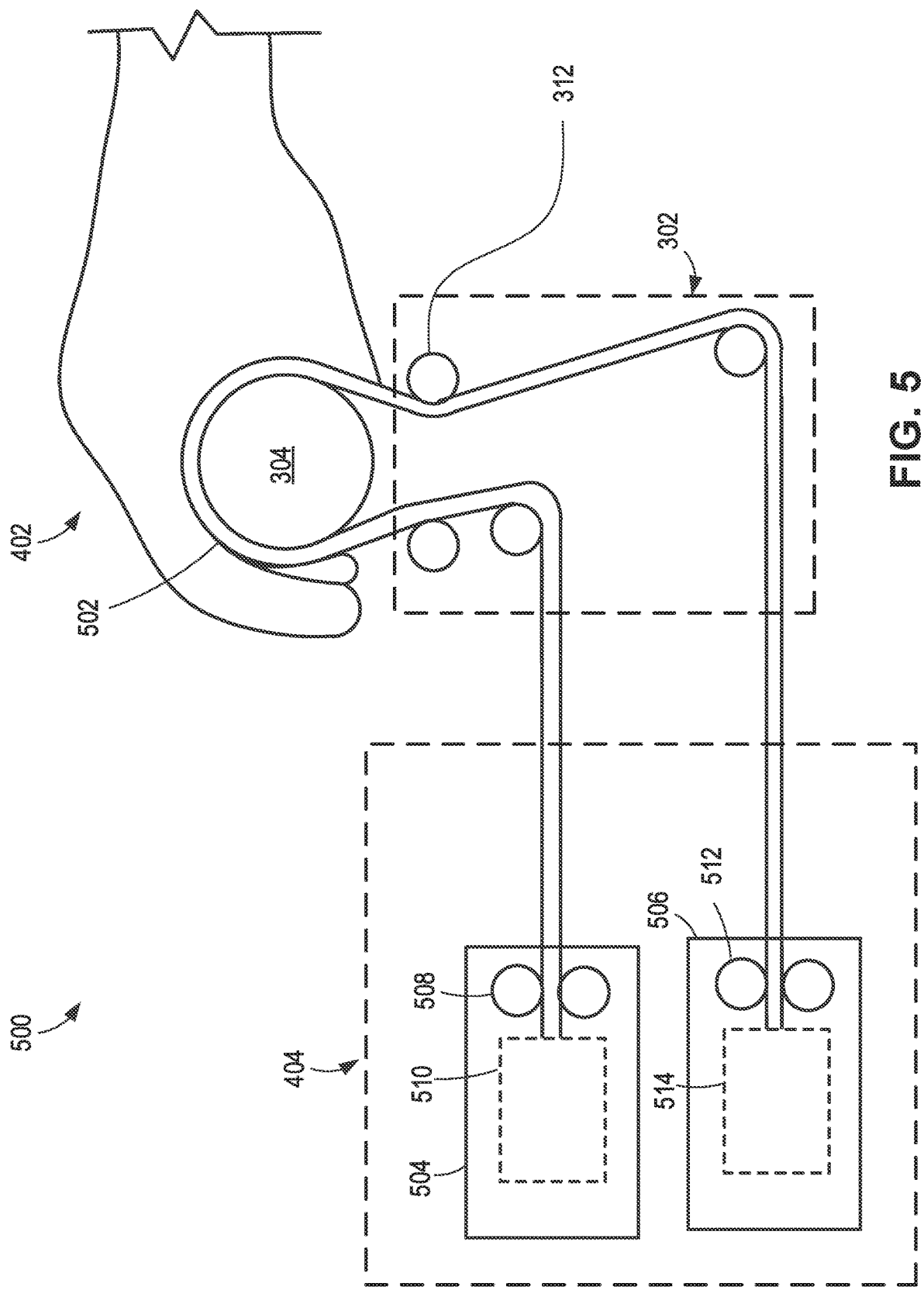
FIG. 5 shows a schematic of a self-cleaning door handle that includes a clean repository and a waste repository.

FIG. 5 shows a self-cleaning door handle 500 according to a second embodiment. The housing 302, rollers 312, and hand grip 304 of self-cleaning door handle 500 are substantially similar to the self-cleaning door handle 300. However, a hygienic film 502 is retrieved from a clean repository 504 and deposited in a waste repository 506. The clean repository 504 includes at least one roller 508 for guiding the hygienic film 502 from a supply of hygienic film 510 to the hand grip 304. The clean repository 504 is configured to store a clean portion of the hygienic film 502 prior to being guided to the hand grip 304 by the plurality of cylindrical rollers 312a-312c. For example, the plurality of cylindrical rollers 312a-312c and/or roller 508 are configured to extract the clean hygienic film 502 from the clean repository 504 when needed.

The clean repository 504 contains a supply of clean hygienic film 510 that is either sanitized before advancing to the hand grip 304, or used as is without additional sanitation (e.g., via a cleaning chamber). For example, in some embodiments, a UV light or sanitization source is provided between the clean repository 504 and the hand grip 304.

At least one roller 508 is in addition to the drive roller of the at least one rollers cylindrical rollers 312a-312c, but in some embodiments at least one roller 508 is not used. The supply of hygienic film 510 is typically in the form of a roll or accordion style stack. In some embodiments, the supply of hygienic film 510 is enough supply for 100-500 refreshes of the hygienic film 502. In some embodiments, when the supply is empty or nearly empty a signal is sent to the vehicle processor to alert the vehicle that a resupply is needed. During servicing, a technician is able to remove an access panel and resupply the supply of hygienic film 510. In some embodiments, the access panel is removed with a proprietary tool so that passengers cannot tamper with the supply of hygienic film 510.

Similarly, the waste repository 506 includes at least one roller 512 and waste container 514 for guiding the hygienic film 502 into the waste container 514 of hygienic film 502 that is advanced via the drive roller from the hand grip 304. In some embodiments, the waste repository 506 is configured to store a contaminated portion of the hygienic film 502 upon being guided away from the hand grip 304 by the plurality of cylindrical rollers 312a-312c. In some embodiments, the contaminated hygienic film 502 is shredded by a shredder in the door handle (not shown) and not-reused. The rollers 312a-312c and/or rollers 512 are configured to deposit the contaminated hygienic film into the waste repository 506 when needed.

The supply of hygienic film 510 is typically in the form of a roll or accordion style stack. In some embodiments, the waste container 514 of hygienic film 502 is large enough to store 100-500 refreshes of the hygienic film 502. In some embodiments, when the waste container 514 of hygienic film 502 is full or nearly full (e.g., as determined by an optical sensor), a signal is sent to the vehicle processor to alert the vehicle or a network-based fleet computer, that the waste container 514 of hygienic film 502 is full and needs to be emptied. During servicing, a technician is able to remove the access panel and empty the waste container 514 of hygienic film 502. In some embodiments, the access panel is a different access panel than the access panel used for the clean repository 504.

Figure 6:
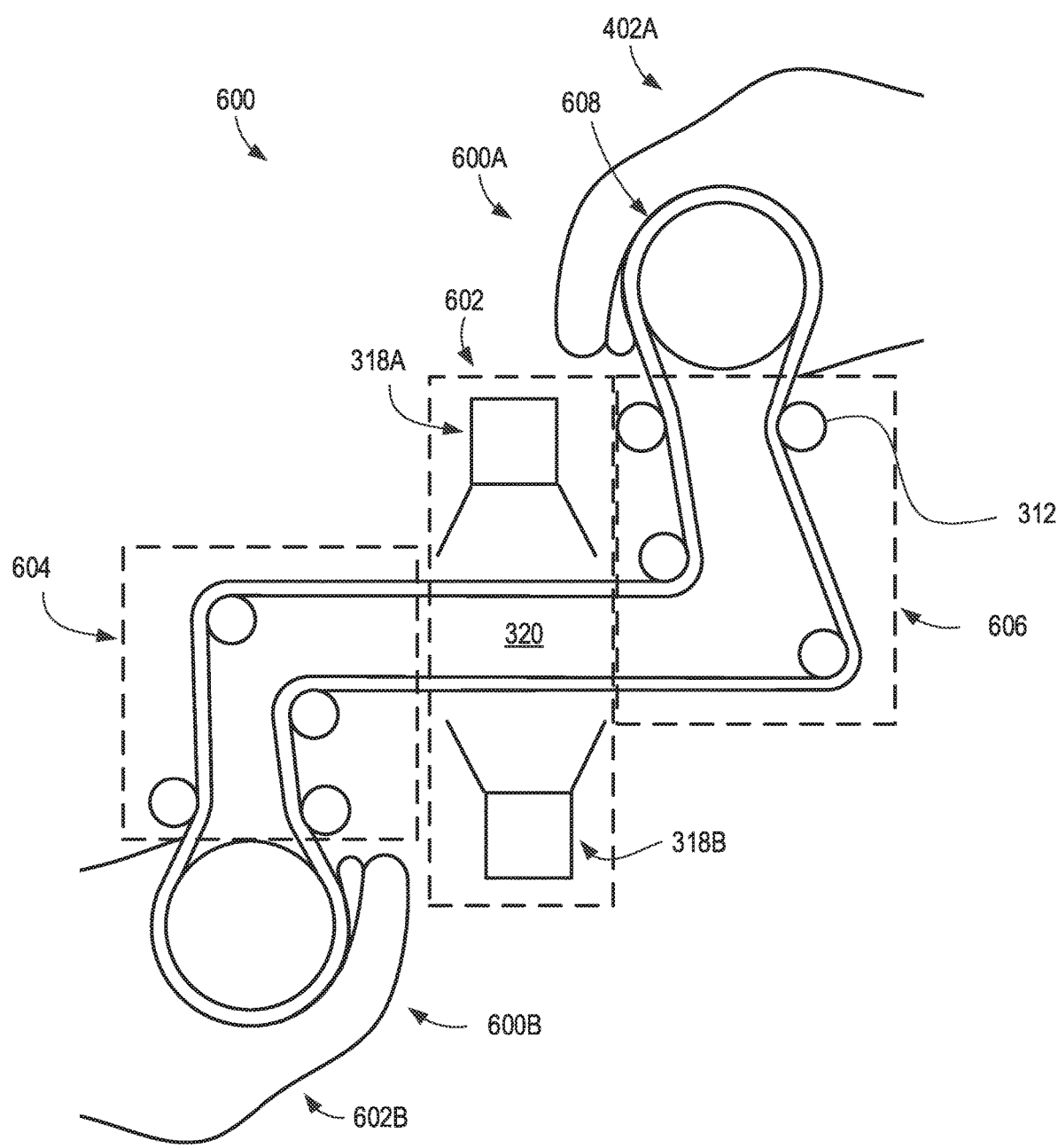
FIG. 6 shows a schematic of a pair of self-cleaning door handles located on each respective side of a vehicle door.

FIG. 6 shows a self-cleaning door handle 600 according to a third embodiment. The housing 302, rollers 312, and hand grip 304 of self-cleaning door handle 600 are substantially similar to the self-cleaning door handle 300. However, the self-cleaning door handle 600 includes a pair of a self-cleaning door handles 600A, 600B and a pair of sanitization sources 318A, 318B that are each identical to the single sanitization source 318 in the first embodiment and located within a cleaning chamber. The self-cleaning door handle 600 is configured to provide a first handle 600A on one side of the vehicle door, and a second handle 600B on the opposite side of the vehicle door. For example, in an embodiment where the first handle 600A is on the exterior of the vehicle door (i.e., outside the vehicle), the second handle 600B is on the inside of the vehicle door (i.e., inside the vehicle). By having two sanitization sources 318A, 318B, a hygienic film 608 wrapped around each hand grip of the respective handle can be refreshed in a continuous loop. Components that are located within the vehicle door itself is represented with region 602. In some embodiments, components of regions 602, 604, 606 are located within the vehicle door. The first handle 600A may be a symmetric copy of the second handle 600B. When the drive roller advances the hygienic film 608, the hygienic film 608 associated with each handle 600A, 600B is refreshed via a cleaning chamber.

Figure 7A:
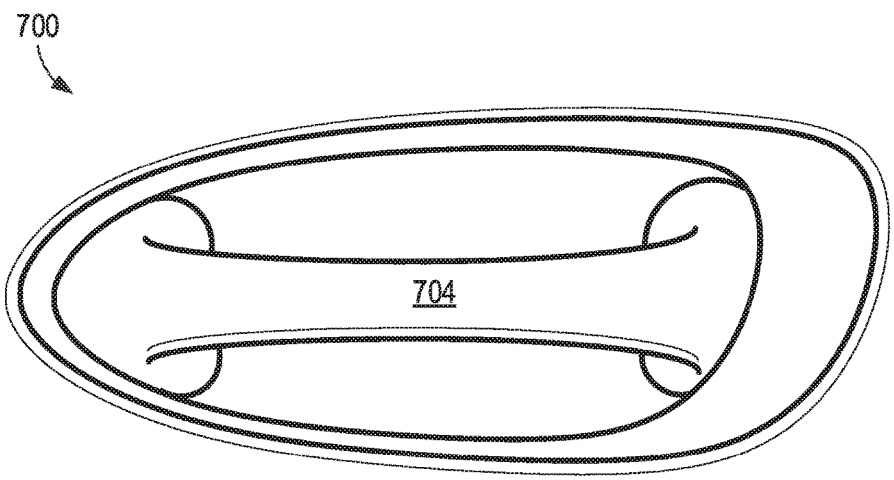
FIG. 7A shows a front view of a door handle with a curved hand grip.
Figure 7B:
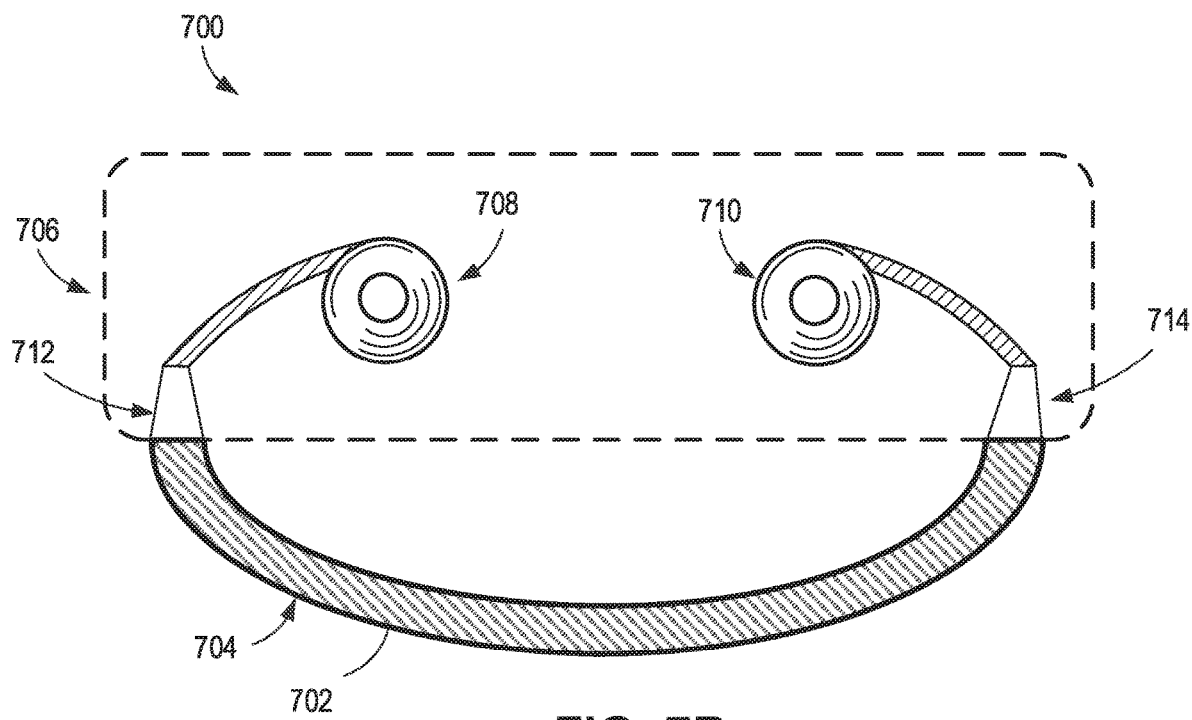
FIG. 7B shows a top view schematic of the door handle of FIG. 7A.

FIGS. 7A-7B show a self-cleaning door handle 700 according to a fourth embodiment. FIG. 7A shows a front view of the self-cleaning door handle 700 and FIG. 7B shows a top view schematic of the self-cleaning door handle 700. The operation of self-cleaning door handle 700 is substantially similar to the self-cleaning door handles previously described. However, instead of a hygienic film traversing around an outer circumference of a hand grip, a hygienic film 702 is configured to traverse along an axial direction of a handle portion 704 in addition to traversing around an outer circumference of the handle portion 704. Handle portion 704 projects from a door 706 of the vehicle in a semi-circular shape. However, in some embodiments, the handle portion 704 is cylindrical. The interior of the door is denoted by region 706.

The self-cleaning door handle 700 includes a roll of clean hygienic film 708 and a roll of waste hygienic film 710 that are housed within the door 706. When the hygienic film surrounding the handle portion 704 is refreshed, a motor attached to the roll 708 (or a drive roller) spins a portion of the roll 708 while a similar motor attached to the roll 710 spins a comparable amount. In this way, the hygienic film 702 traverses around the self-cleaning door handle 700 in a counter-clockwise rotation (as viewed from an observer viewing FIG. 7B on the page).

The self-cleaning door handle 700 includes transition regions 712, 714 associated with each roll 708, 710 that transitions the hygienic film 702 from a roll form to a form that can be wrapped around the entire circumference of the handle portion 704. In this way, the hygienic film 702 traverses around a longitudinal direction of the handle portion 704.

The self-cleaning door handle 700 can also include one or more cleaning chamber to sanitize the hygienic film 702 prior to, or after, being used.

Figure 8:
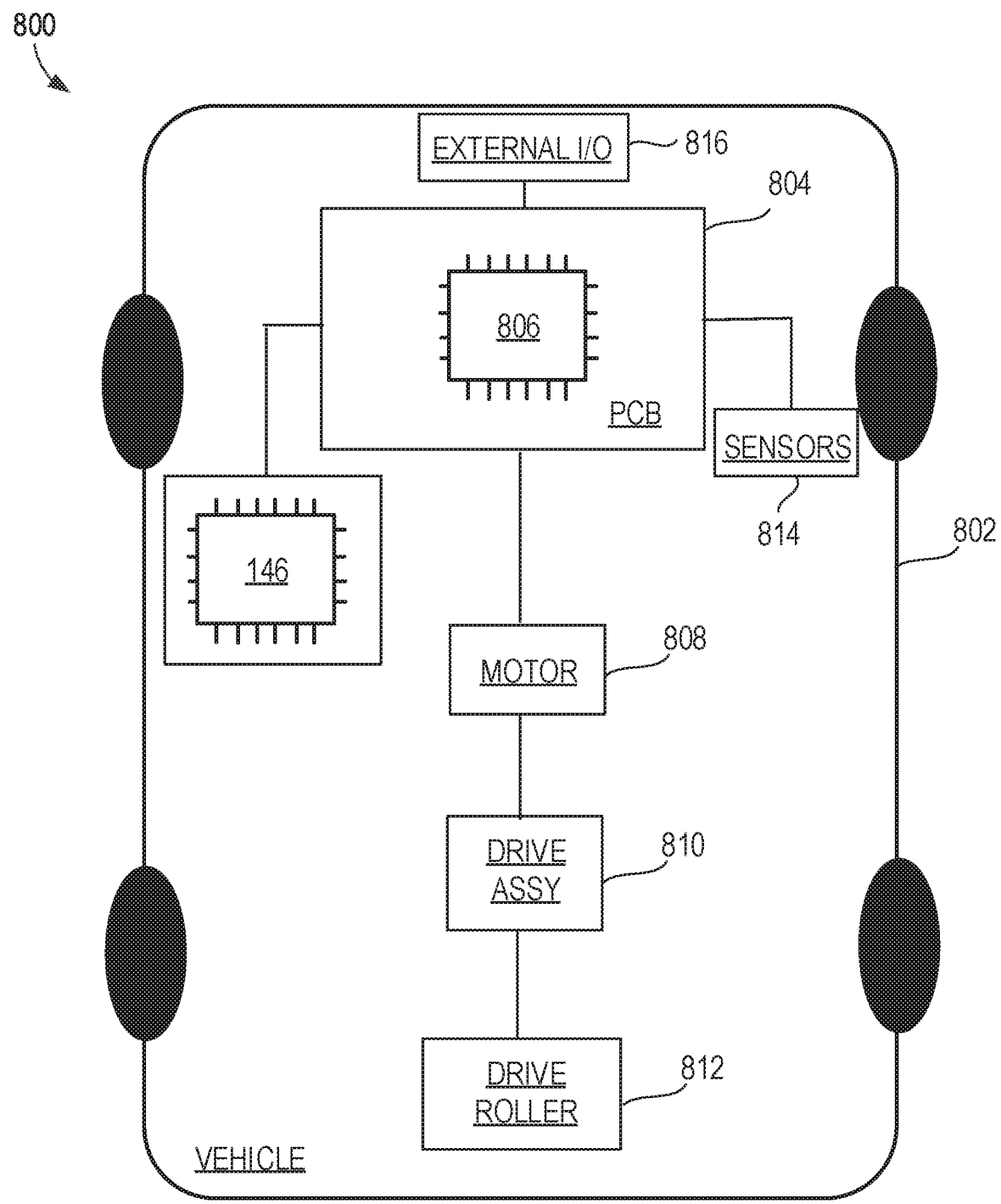
FIG. 8 is block diagram illustrating a control system for self-cleaning door handles, according to one or more embodiments.

FIG. 8 shows a system 800 associated with a self-cleaning door handle according to one or more embodiments described in this specification. As previously mentioned, the door handles include but are not limited to: a cleaning chamber where UV light and/or chemical sanitizing agents are applied, a waste repository for storing used or shredded film (e.g., for embodiments that destroy the film rather than sanitize the film), one or more rotatable drive rollers, one or more optional rotatable and/or fixed film guides for dispensing/guiding new film and/or taking up sanitized film that exits the cleaning-chamber, an optional film shredding subsystem included in or coupled the waste repository, one or more motors (e.g., DC, stepper) for driving the drive roller, one or more gear or drive assemblies (e.g., reduction gears) mechanically coupling the one or more motors to the one or more drive rollers and one or more printed circuit boards (PCBs) that include a processor, or microcontroller (e.g., a 16-bit PIC24 MCU with integrated CAN developed by Microchip Technology Inc.) for controlling the entire cleaning process using open or closed-feedback control.

Referring to FIG. 8, a processor or microcontroller 806 is located on a PCB 804 within a vehicle 802. The vehicle 802 is substantially similar to the AV 100, but can also be semi-autonomous or non-autonomous. The PCB 804 can include other electrical and power regulation components, such as a voltage regulator, power management chip, etc.).

The system 800 includes one or more peripherals for interfacing with one or more motors 808 and one or more sensors 814 used in the cleaning process (e.g., optical or proximity sensors for closed loop feedback control) and an input/output (I/O) interface 816 for a vehicle control area network (CAN) bus or Ethernet for receiving, for example, cleaning commands, from a vehicle processor (e.g., processor 146), and reporting by the microcontroller a cleaning process status, failures, etc., to the vehicle processor 146 so that the vehicle processor 146 can initiate various actions (e.g., starting/stopping cleaning process, locking/unlocking doors, etc.). The sensors 814 enable closed loop or open loop feedback control of a drive roller 812 or a set of drive rollers.

The one or more motors 808 convert electrical energy supplied from a battery within the vehicle into rotation. The rotation is mechanically coupled to the drive roller 812 via a drive assembly 810 (e.g., by a set of gears, a belt, a rotational coupler, etc.). The drive roller 812 frictionally engages the hygienic film to advance it for cleaning or disposal. As previously mentioned, in some embodiments, the drive roller is part of a set of cylindrical rollers, or it can be part of the hand grip itself.

Figure 9:
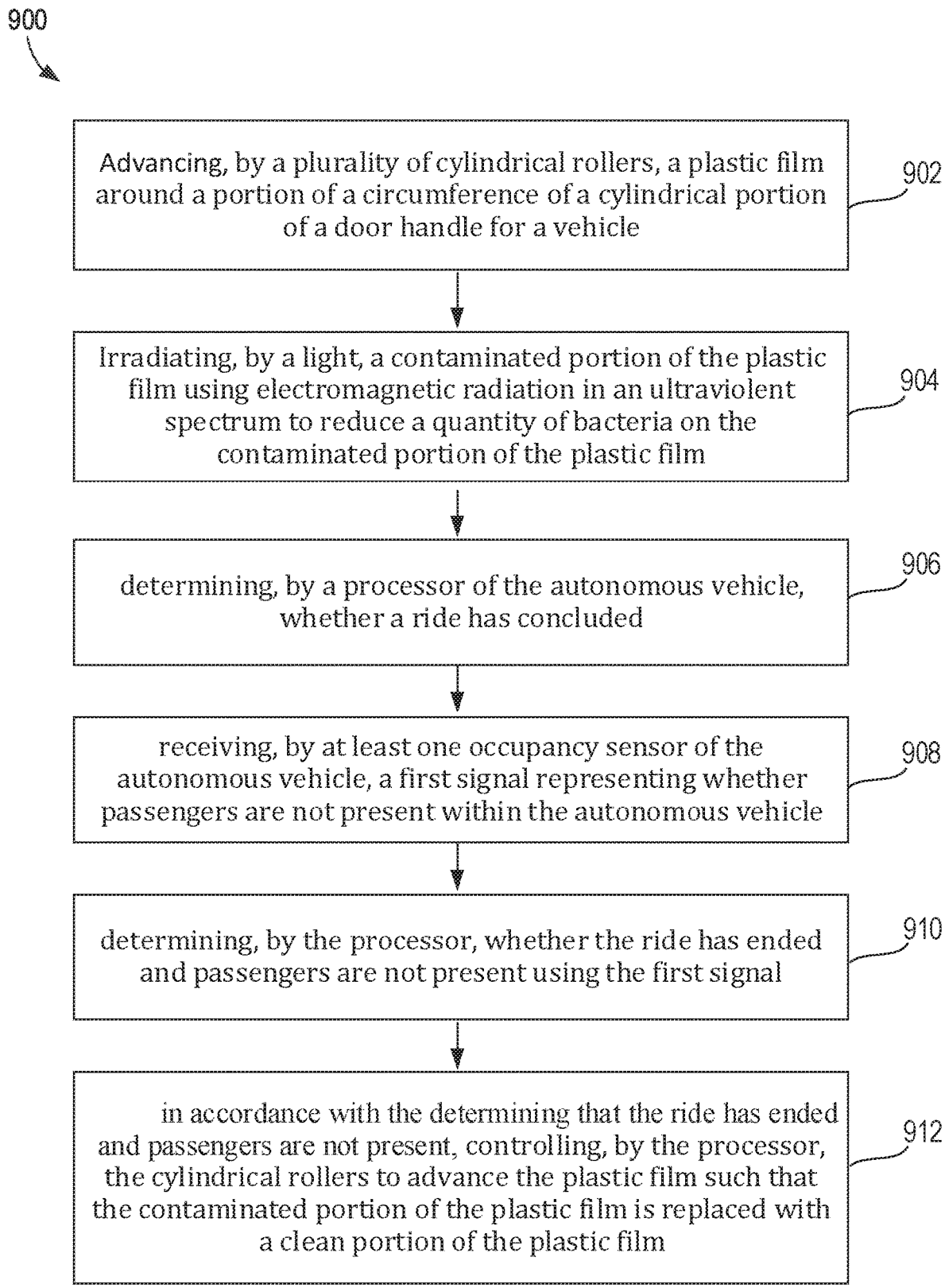
FIG. 9 shows a flow chart of an operation of the self-cleaning door handles, according to one or more embodiments.

FIG. 9 shows a flow chart of an operation 900 of the self-cleaning door handles according to any of the embodiments described in this specification.

A plurality of cylindrical rollers advance (902) a hygienic film around a portion of a circumference of a hand grip of a door handle for a vehicle. A light irradiates (904) a contaminated portion of the hygienic film using electromagnetic radiation in an ultraviolet spectrum to reduce a quantity of bacteria on the contaminated portion of the hygienic film.

In some embodiments, a processor of the autonomous (or non-autonomous, or semi-autonomous) vehicle determines (906) whether a ride has concluded. For example, when the vehicle is an autonomous vehicle (e.g., AV 100), the AV 100 knows when the ride is complete (e.g., when it has reached its destination by a map).

In some embodiments, a vehicle processor receives (908) by at least one occupancy sensor of the vehicle, a first signal representing whether passengers are not present within the vehicle. For example, when the sensors (e.g., sensors 121 of AV 100) are configured as weight sensors associated with each seat of the vehicles measures whether a passenger is sitting on the respective seat. In some cases, when the sensors 121 are configured as a camera, IR sensor, or thermal imaging camera can tell whether passengers are present and not present within the vehicle.

In some embodiments, the vehicle controller determines (910) whether the ride has ended and passengers are not present using the first signal. For example, a face detection algorithm can be used to determine if passengers are present within the vehicle and a map can be queried to determine if the ride has reached its destination.

In some embodiments, in accordance with the determining that the ride has ended and passengers are not present, the vehicle processor controls (912) the cylindrical rollers to advance the hygienic film such that the contaminated portion of the hygienic film is replaced with a clean portion of the hygienic film.

In some embodiments, the vehicle processor receives, by at least one door sensor of the vehicle, a second signal representing whether all doors of the vehicle are closed and the vehicle processor determines whether the ride has ended and all doors are closed using the second signal. In this case, the controlling of the cylindrical rollers occurs when all doors of the vehicle are closed as determined by the vehicle processor.

In some embodiments, in accordance with the determining that the ride has ended and all doors are closed, the vehicle processor is further configured for controlling the light to irradiate the contaminated portion of the hygienic film.

In some embodiments, the plurality of cylindrical rollers advances a clean portion of the hygienic film from a first repository to the hand grip.

In some embodiments, the plurality of cylindrical rollers advances the contaminated portion of the hygienic film from the hand grip to a second repository.

In some embodiments, the plurality of cylindrical rollers advances, the contaminated portion of the hygienic film from the hand grip, to the light, and back to the hand grip.

The techniques also include a non-transitory computer-readable storage medium including at least one program for execution by at least one processor of a first device, the at least one program including instructions which, when executed by the at least one processor, cause the first device to perform any of the methods described in this specification.

In the foregoing description, embodiments of the invention have been described with reference to numerous specific details that may vary from implementation to implementation. The description and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction. Any definitions expressly set forth herein for terms contained in such claims shall govern the meaning of such terms as used in the claims. In addition, when we use the term "further comprising," in the foregoing description or following claims, what follows this phrase can be an additional step or entity, or a sub-step/sub-entity of a previously-recited step or entity.

What is claimed is:

1. A door handle for a vehicle, the door handle comprising:
   a housing including a hand grip;
   a hygienic film that is formed around a portion of a circumference of the hand grip;
   a plurality of cylindrical rollers rotatably connected to the housing and configured to rotationally guide the hygienic film in a circumferential path around a longitudinal axis of the hand grip along the portion of the circumference of the hand grip such that the hygienic film rotates around the longitudinal axis of the hand grip in the circumferential path; and
   a light that is configured to emit electromagnetic radiation in an ultraviolet spectrum and configured to irradiate at least one portion of the hygienic film to reduce a quantity of bacteria on the at least one portion of the hygienic film.

2. The door handle of claim 1, wherein the light is configured to irradiate the at least one portion of the hygienic film upon being guided away from the hand grip by the plurality of cylindrical rollers.

3. The door handle of claim 1, wherein the cylindrical rollers are configured to advance the hygienic film such that a contaminated portion of the hygienic film is retracted within the housing and irradiated with light to reduce the quantity of bacteria on the contaminated portion of the hygienic film.

4. The door handle of claim 1, wherein the cylindrical rollers are configured to advance the hygienic film such that a clean portion of the hygienic film is supplied from within the housing and guided to the hand grip to replace a contaminated portion of the hygienic film.

5. The door handle of claim 1, wherein the light is configured to irradiate the at least one portion of the hygienic film within a hermetically sealed compartment.

6. The door handle of claim 1, wherein the housing is rigidly attached to a door of the vehicle.

7. The door handle of claim 1, wherein the hygienic film is a closed roll.

8. The door handle of claim 1, further comprising a first repository configured to store a clean portion of the hygienic film prior to being guided to the hand grip by the plurality of cylindrical rollers.

9. The door handle of claim 8, further comprising a second repository configured to store a contaminated portion of the hygienic film upon being guided away from the hand grip by the plurality of cylindrical rollers.

10. The door handle of claim 1, wherein the cylindrical rollers are configured to advance the hygienic film in response to a processor of the vehicle determining that a passenger's ride has concluded and that the passenger has exited the vehicle.

11. The door handle of claim 1, further comprising an end cap that covers an edge of the hygienic film.

12. The door handle of claim 1, wherein the light is mounted within the housing.

13. A method comprising:
    advancing, by a plurality of cylindrical rollers, a hygienic film in a circumferential path around a longitudinal axis of a hand grip of a door handle for a vehicle and around a portion of a circumference of the hand grip of the door handle for the vehicle such that the hygienic film circumferentially rotates around the longitudinal axis of the hand grip in the circumferential path; and
    irradiating, by a light mounted within the door handle, a contaminated portion of the hygienic film using electromagnetic radiation in an ultraviolent spectrum to reduce a quantity of bacteria on the contaminated portion of the hygienic film.

14. The method of claim 13, further comprising:
    determining, by a processor of the vehicle, whether a ride has concluded;
    receiving, by at least one occupancy sensor of the vehicle, a first signal representing whether passengers are not present within the vehicle;
    determining, by the processor, whether the ride has ended and passengers are not present using the first signal; and
    in accordance with the determining that the ride has ended and passengers are not present, controlling, by the processor, the cylindrical rollers to advance the hygienic film such that the contaminated portion of the hygienic film is replaced with a clean portion of the hygienic film.

15. The method of claim 14, further comprising
    receiving, by at least one door sensor of the vehicle, a second signal representing whether all doors of the vehicle are closed;
    determining, by the processor, whether the ride has ended and all doors are closed using the second signal; and
    wherein the controlling of the cylindrical rollers occurs when all doors of the vehicle are closed as determined by the processor.

16. The method of claim 15, wherein in accordance with the determining that the ride has ended and all doors are closed, the processor is further configured for controlling the light to irradiate the contaminated portion of the hygienic film.

17. The method of claim 13, further comprising:
advancing, by the plurality of cylindrical rollers, a clean portion of the hygienic film from a first repository to the hand grip.

18. The method of claim 17, further comprising:
advancing, by the plurality of cylindrical rollers, the contaminated portion of the hygienic film from the hand grip to a second repository.

19. The method of claim 13, further comprising:
advancing, by the plurality of cylindrical rollers, the contaminated portion of the hygienic film from the hand grip, to a hermetically sealed compartment including the light, and back to the hand grip.

20. A non-transitory computer-readable storage medium comprising at least one program for execution by at least one processor of a first device, the at least one program including instructions which, when executed by the at least one processor, cause the first device to perform operations comprising:
advancing, by a plurality of cylindrical rollers, a hygienic film in a circumferential path around a longitudinal axis of a hand grip of a door handle for a vehicle and around a portion of a circumference of the hand grip of the door handle for the vehicle such that the hygienic film circumferentially rotates around the longitudinal axis of the hand grip in the circumferential path; and
irradiating, by a light mounted within the door handle, a contaminated portion of the hygienic film using electromagnetic radiation in an ultraviolet spectrum to reduce a quantity of bacteria on the contaminated portion of the hygienic film.

\* \* \* \* \*

UNITED STATES PATENT AND TRADEMARK OFFICE
CERTIFICATE OF CORRECTION

| | | |
|---|---|---|
| PATENT NO. | : 11,684,684 B2 | Page 1 of 1 |
| APPLICATION NO. | : 17/012043 | |
| DATED | : June 27, 2023 | |
| INVENTOR(S) | : Daniele De Francesco | |

It is certified that error appears in the above-identified patent and that said Letters Patent is hereby corrected as shown below:

On the Title Page

Item (57), Column 2 (Abstract), Line 9, delete "ultraviolent" and insert -- ultraviolet --;

In the Claims

Column 18, Line 39, in Claim 13, delete "ultraviolent" and insert -- ultraviolet --; and Column 20, Line 14, in Claim 20, delete "ultraviolent" and insert -- ultraviolet --.

Signed and Sealed this
Seventh Day of November, 2023

*Katherine Kelly Vidal*

Katherine Kelly Vidal
*Director of the United States Patent and Trademark Office*